(12) United States Patent
Peckham

(10) Patent No.: US 8,092,541 B2
(45) Date of Patent: Jan. 10, 2012

(54) METHOD OF USING AN ANTI-GROWTH MATRIX AS A BARRIER FOR CELL ATTACHMENT AND OSTEO-INDUCTIVE FACTORS

(75) Inventor: Steven M. Peckham, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 966 days.

(21) Appl. No.: 11/833,651

(22) Filed: Aug. 3, 2007

(65) Prior Publication Data

US 2009/0036988 A1 Feb. 5, 2009

(51) Int. Cl.
*A61F 2/44* (2006.01)
(52) U.S. Cl. ............ 623/17.16; 623/17.11; 606/279
(58) Field of Classification Search .... 623/17.11–17.16; 606/279
See application file for complete search history.

(56) References Cited

U.S. PATENT DOCUMENTS

| | | | |
|---|---|---|---|
| 5,534,028 A | 7/1996 | Bao et al. | |
| 5,645,597 A | 7/1997 | Krapiva | |
| 5,752,930 A | 5/1998 | Rise et al. | |
| 5,976,186 A | 11/1999 | Bao et al. | |
| 6,001,386 A | 12/1999 | Ashton et al. | |
| 6,007,843 A | 12/1999 | Drizen | |
| 6,187,048 B1 | 2/2001 | Milner et al. | |
| 6,371,990 B1 | 4/2002 | Ferree | |
| 6,416,776 B1 | 7/2002 | Shamie | |
| 6,454,804 B1 | 9/2002 | Ferree | |
| 6,551,290 B1 | 4/2003 | Eisberry et al. | |
| 6,571,125 B2 | 5/2003 | Thompson | |
| 6,594,880 B2 | 7/2003 | Eisberry et al. | |
| 6,599,526 B2* | 7/2003 | Dimitrijevich | 424/448 |
| 6,969,404 B2 | 11/2005 | Ferree | |
| 7,094,258 B2 | 8/2006 | Lambrecht et al. | |
| 7,318,840 B2* | 1/2008 | McKay | 623/17.11 |
| 2002/0082583 A1 | 6/2002 | Lerner | |
| 2003/0185874 A1* | 10/2003 | Calhoun et al. | 424/426 |
| 2004/0064088 A1 | 4/2004 | Gorman et al. | |
| 2004/0065615 A1 | 4/2004 | Hooper et al. | |
| 2004/0082908 A1 | 4/2004 | Whitehurst et al. | |
| 2004/0096422 A1* | 5/2004 | Schwartz et al. | 424/78.37 |
| 2004/0098113 A1 | 5/2004 | Forsell et al. | |
| 2004/0106914 A1 | 6/2004 | Coppeta et al. | |
| 2005/0074453 A1* | 4/2005 | Ferree | 424/145.1 |
| 2005/0143817 A1* | 6/2005 | Hunter et al. | 623/11.11 |
| 2005/0149080 A1* | 7/2005 | Hunter et al. | 606/155 |
| 2005/0149158 A1* | 7/2005 | Hunter et al. | 607/119 |
| 2005/0165488 A1* | 7/2005 | Hunter et al. | 623/17.16 |
| 2005/0175663 A1* | 8/2005 | Hunter et al. | 424/423 |
| 2005/0175665 A1* | 8/2005 | Hunter et al. | 424/423 |

(Continued)

OTHER PUBLICATIONS

Rapp, Susan M., New anti-adhesion gel could help make spine revision surgery easier, Apr. 2006, OrthoSuperSite, http://www.orthosupersite.com/view.aspx?rid=16436.*

*Primary Examiner* — Eduardo C Robert
*Assistant Examiner* — Ellen C Hammond

(57) ABSTRACT

The present invention generally relates to a method of using a matrix as a barrier for unwanted cell attachment and bone formation in unwanted areas of the human body during implant procedures. More specifically, a growth-inhibiting matrix may be used to prevent migration of osteo-inductive agents or bone tissue from an intervertebral disc space through the outer bands of annulus fibrosis that abuts the spinal tissue, canal, and other surrounding areas.

11 Claims, 2 Drawing Sheets

U.S. PATENT DOCUMENTS

| | | | |
|---|---|---|---|
| 2005/0175703 A1* | 8/2005 | Hunter et al. | 424/486 |
| 2005/0177225 A1* | 8/2005 | Hunter et al. | 623/1.42 |
| 2005/0178395 A1* | 8/2005 | Hunter et al. | 128/898 |
| 2005/0178396 A1* | 8/2005 | Hunter et al. | 128/898 |
| 2005/0181008 A1* | 8/2005 | Hunter et al. | 424/423 |
| 2005/0181011 A1* | 8/2005 | Hunter et al. | 424/423 |
| 2005/0181977 A1* | 8/2005 | Hunter et al. | 514/2 |
| 2005/0182463 A1* | 8/2005 | Hunter et al. | 607/115 |
| 2005/0183728 A1* | 8/2005 | Hunter et al. | 128/207.14 |
| 2005/0183731 A1* | 8/2005 | Hunter et al. | 128/898 |
| 2005/0186244 A1* | 8/2005 | Hunter et al. | 424/423 |
| 2005/0187140 A1* | 8/2005 | Hunter et al. | 514/2 |
| 2005/0191331 A1* | 9/2005 | Hunter et al. | 424/423 |
| 2005/0196421 A1* | 9/2005 | Hunter et al. | 424/423 |
| 2005/0208095 A1* | 9/2005 | Hunter et al. | 424/423 |
| 2006/0147492 A1* | 7/2006 | Hunter et al. | 424/426 |
| 2006/0229728 A1* | 10/2006 | McKay | 623/17.16 |
| 2007/0020314 A1* | 1/2007 | Haro et al. | 424/443 |
| 2007/0100348 A1* | 5/2007 | Cauthen et al. | 606/99 |
| 2007/0208134 A1* | 9/2007 | Hunter et al. | 525/54.1 |
| 2007/0299043 A1* | 12/2007 | Hunter et al. | 514/171 |
| 2008/0019970 A1* | 1/2008 | Gorman | 424/141.1 |
| 2009/0226500 A1* | 9/2009 | Avelar et al. | 424/423 |
| 2009/0226503 A1* | 9/2009 | Haro et al. | 424/423 |
| 2010/0028309 A1* | 2/2010 | Odar et al. | 424/93.7 |

* cited by examiner

METHOD OF USING AN ANTI-GROWTH MATRIX AS A BARRIER FOR CELL ATTACHMENT AND OSTEO-INDUCTIVE FACTORS

FIELD OF INVENTION

The present invention generally relates to a method of using a matrix as a barrier for unwanted cell attachment and bone formation. More specifically, there is disclosed the use of a growth-inhibiting matrix to prevent migration of osteo-inductive agents or bone tissue from an intervertebral disc space through the outer bands of annulus fibrosis that abuts the spinal tissue and canal and other surrounding areas.

BACKGROUND OF THE INVENTION

The human spine is a complex arrangement of connective tissue, vertebrae, intervertebral discs, the spinal canal, the spinal cord, nerves, and the like. A plurality of vertebrae are stacked upon one another into four regions, the cervical, thoracic, lumbar, and sacrum regions. Intervertebral discs are located between stacked vertebra and abut the spinal cord, which runs through the spinal canal of the vertebrae.

Healthy intervertebral discs make the spine remarkably strong and flexible, being able to bend with ease when under heavy loads. The intervertebral discs have several functions, one of which is serving as shock absorbers for the spine. Each disc resembles a jelly donut, having a relatively tough outer layer, called the annulus fibrosis, that surrounds a gel-like inner layer, called that nucleus pulposus. The annulus fibrosis is composed of concentric layers of intertwined fibrocartilage forming annular bands, which are arranged to resist forces placed upon the spine. The vertebrae's cartilaginous endplate, also a part of the disc space, separates the nucleus pulposus and annulus fibrosis from the adjacent vertebrae.

The nucleus pulposus is composed of cells from the primitive notochord and contains significant amounts of substances capable of exciting, or increasing the excitability of, sensory nerves. These substances include prostaglandin E, histamine-like substances, potassium ions, lactic acid, and several polypeptide amines.

Although the spine is resilient, trauma or osteo-degenerative diseases can cause injury to vertebrae or intervertebral discs, particularly about the lumbar region of the spine. This is a source of chronic lower back pain for millions of people. Tears to the intervertebral discs can lead to herniated disc disease, where the nucleus pulposus migrates into the outer areas of the intervertebral disc space and presses against the spinal cord or possibly collapses vertebral bodies onto one another. Herniated discs or tears in the annulus fibrosis can make the slightest movements very painful.

There are many ways to treat intervertebral disc problems. Current methods focus on fusing adjacent vertebrae together or using partial or total prosthetic disc implants. In a spinal fusion procedure, some or all of the disc material is removed from the level to be fused. In particular, for interbody fusion procedures such as posterior lumbar interbody fusions (PLIF) or transforaminal lumbar interbody fusions (TLIF), a hole is made in the annulus and the interior portion of the disc is removed. Cartilaginous endplates are abraded to induce bleeding bone. In the place of disc material, an interbody fusion device is implanted. The fusion device is intended to maintain the height of the disc space and help stabilize the segment while fusion occurs. Fusion is achieved by implanting either bone harvested from another site in the patient (autograft) or an autograft replacement into the disc space.

Autograft replacement implants are associated with osteo-inductive factors and other bio-active agents that help promote osteoblastic formation. The ultimate goal of these implants is to promote bone growth that will connect vertebrae endplates to limit motions associated with the patient's lower back pain.

There are potential drawbacks to these sorts of spinal procedures. The surgically made hole in the outer band of the annulus fibrosis, if not properly closed or shielded, could act as a door for bone tissue and osteo-inductive agents to migrate from the intervertebral disc space into the area about the spinal canal. These migrations could eventually lead to pain in the patient associated with bone tissue protruding through the annulus fibrosis and pressing against spinal nerves.

Another possibility is bone tissue forming about the spinal canal due to osteo-inductive agents that have passed through the outer bands of annulus fibrosis. Depending on the type and amount of osteo-inductive agent used in the procedure, one could have bone or cartilage forming about the spinal cord, nerve roots, and surrounding muscles that can cause severe pain.

The prior art discloses methods or devices dealing with closing surgically prepared holes in the annulus fibrosis. U.S. Pat. No. 7,094,258 discloses methods of reinforcing the annulus fibrosis. The '258 patent further discloses inserting a barrier into the interior of an annular defect to seal it after an implant procedure. This patent prefers that the barrier be flexible in nature, being made from woven material such as Dacron™ fabric, Nylon™ fabric, collagen, synthetic polymers, and the like.

U.S. Pat. No. 6,371,990 discloses an apparatus and method for controlling vertebral motion. The '990 patent discloses reinforcing the inner walls of annulus fibrosis to support a prosthetic disc implant. The opening in the annulus fibrosis, referred in the '990 patent as flaps, is sewn shut and supported by a wire mesh that is screwed into adjacent vertebrae separated by the targeted disc space.

U.S. Pat. No. 6,454,804 discloses using a mixture of living annulus fibrosis tissue and the same obtained from a recently deceased person or animal donors to augment damaged annulus fibrosis in a patient. The '804 patent generally refers to gluing or suturing this annulus mixture to the inside or the outside of a patient's annulus.

Despite these procedures, there remains a need for a method that uses a tissue inhibiting matrix to ease complications associated with cell and osteo-inductive agent migration in the early phases of spinal repair.

SUMMARY OF THE INVENTION

The present invention overcomes the drawbacks of prior art by providing a novel method for preventing bone migration into soft tissue regions. Generally, a barrier is placed in the body between a first region and a second region. The barrier prevents migration of cells associated with the first region, for example osteoblastic cells, from migrating into soft tissue located about a second region.

A specific embodiment provides for a method which includes repairing an intervertebral disc. The method comprises forming a hole in the annulus fibrosis; removing damaged annulus fibrosis or nucleus pulposus from the intervertebral disc space; inserting an intervertebral disc implant into the emptied disc space; and closing the hole formed in the annulus fibrosis by delivering a growth-inhibiting matrix in or about the surfaces of the hole, such that the matrix acts as a barrier that prevents new tissue or agents associated with the implant from migrating into areas outside the intervertebral disc space. The new tissue may be, for example, bone.

In various embodiments, the method includes a matrix that cures in vivo.

In certain embodiments, the method includes a matrix that inhibits cells associated with the selected tissue type from attaching onto or into the inner surfaces of the growth-inhibiting matrix exposed to the center of the targeted implant region, such as the intervertebral disc space.

In certain other embodiments, the matrix inhibits the migration of osteo-inductive agents associated with the intervertebral implant from migrating into areas outside the targeted implant region, such as the intervertebral disc space.

In certain preferred embodiments, agents are associated with the intervertebral disc implant. The agents include at least one osteogenic agent selected from the group consisting of BMP (bone morphogenetic protein), BMP-2 (bone morphogenetic protein), bFGF (basic fibroblast growth factor), (insulin-like growth factor), PDGF (platelet-derived growth factor), rhBMP (human recombinant bone morphogenetic protein), TGF-β1 (transforming growth factor beta 1), VEGF (vascular endothelial growth factor), GDF (growth and differentiation factors), and any combinations thereof.

In other preferred embodiments, the matrix comprises at least one osteogenic protein-binding antibody selected from the group consisting of anti-BMP, anti-BMP-2, anti-bFGF, anti-IGF-1, anti-PDGF, anti-rhBMP, anti-TGF-β1, anti-VEGF, anti-GDF, and any combinations thereof.

In certain specific embodiments, at least one matrix osteogenic inhibitory agent is embedded into a bio-resorbable material and is time released.

In particular embodiments, the matrix prevents cells and osteogenic factors from migrating into areas outside the intervertebral disc space but allows fluid passage between the two.

In specific embodiments, the matrix is made from an anti-adhesion material that may or may not cure in vivo. The anti-adhesion material may include hyaluronic acid, carboxy methyl cellulose, gelatin, hydrogels, collagen gels, synthetic polymer formulations, or combinations thereof.

In other specific embodiments, the matrix further comprises an effective amount of at least one bioactive molecule capable of inhibiting cell attachment to the outer and inner surfaces of the matrix that is exposed to the implant or annulus fibrosis that is located in the disc space. The bioactive molecule capable of inhibiting cell attachment may comprise one or more anionic polymers such as, for example, dextran sulfate.

In some embodiments, the matrix may be delivered by injection into or about the hole in the annulus fibrosis that extends from the outer bands of the annulus fibrosis of an intervertebral disc into the areas in or about the nucleus pulposus located near the center of the intervertebral disc space. The matrix may be delivered to the hole by a syringe, needle, cannula, catheter, pump, or any similar device, or any combination thereof.

In certain specific embodiments, the growth-inhibiting matrix is bioresorbable within 2 to 6 weeks from delivery to the hole. Suitable materials include resorbable hydrogels, resorbable polymer compositions, resorbable copolymer compositions, resorbable polyion complexes, fibrin, collagen, gelatin, alginate, hyaluronate, Matrigel® membrane preparation, polyglycolide (PGA), glycolide-lactide copolymers (PGLA), polylactides (PLA), poly-L-lactide (PLLA), poly-D,L-lactide (PDLLA), ethylene oxide block copolymers with PLA, ethylene oxide block copolymers with propylene oxide chains, and combinations thereof.

In some embodiments, the implant is made from materials selected from the group consisting of polyethylene glycol (PEG), polylactides (PLA), polyglycolide-lactide copolymer (PLGA), polyvinyl alcohol (PVA), collagen sponge, gelatin, gelatin sponge, collagen, fibrin gel, and combinations thereof.

Another aspect provides a kit comprising a composition capable of forming a growth-inhibiting matrix and an implant. In some preferred embodiments, the implant is an intervertebral disc implant. The kit may further comprise a delivery device to deliver the growth-inhibiting matrix. The delivery device may be a syringe, needle, cannula, catheter, pump, any similar device, or any combination thereof. In some embodiments, the kit further comprises an osteogenic inhibitory agent for the growth-inhibiting matrix. In other embodiments, the kit further comprises a bioactive molecule capable of preventing cell attachment to the growth-inhibiting matrix. In yet other embodiments, the kit further comprises an effective amount of a bioactive molecule, associated with the implant, that is capable of inducing cell growth, cell migration, or cell attachment.

DETAILED DESCRIPTION OF THE INVENTION

Definitions

The terms "Growth-inhibiting matrix" and "matrix" refer to a collection of materials that may cure in vivo and act as a barrier against cellular attachment and migration of growth factors, such as osteo-inductive factors.

The terms "Surgically prepared hole" and "hole" refer to holes made in or about surgical target areas, for example a hole made in the outer bands of annulus fibrosis that extends into the area about the nucleus pulposus of an intervertebral disc.

The term "Interbody device" refers to a part of an intervertebral implant that is associated with promoting bone formation via osteo-inductive factors.

The term "Implant" refers to any object that is designed to be placed partially or wholly within a patient's body for healing purposes or artificial structural support, for example intervertebral disc implants and the like. The object is placed in the body and may be made from biologically compatible materials (e.g., medical-grade stainless steel, titanium, and other metals; polymers such as polyurethane, silicon, polylactic acid (PLA), polyglycolic acid (PLGA); and other materials); other materials that are exogenous, some materials derived from animals (e.g., "xenografts" such as whole animal organs; animal tissues such as heart valves; naturally occurring or chemically-modified molecules such as collagen, hyaluronic acid, proteins, carbohydrates, and others); human donor tissues (e.g., "allografts" such as whole organs; tissues such as bone grafts, skin grafts, and others); or from the patients themselves (e.g., "autografts" such as saphenous vein grafts, skin grafts, tendon/ligament/muscle transplants).

From this point, various embodiments of the invention are described. Although the present methods are primarily intended to prevent migration of bone tissue or osteo-inductive agents from the intervertebral disk space into the outer bands of the annulus fibrosis and the areas of the spinal canal surrounding the spinal cord, there are no intentions for the use of these words to limit the scope of the invention for uses in the human body. Any and all use of specific language and references are simply for detailing different embodiments of the same.

In addition, and despite explicit reference to only the following embodiments, any and all alterations and further modifications of the invention, as would occur to one having ordinary skill in the art, are intended to be within the scope of the invention. A non-limiting example is the prevention of tissue adhesion ingrowth about the spinal area after spinal fusion procedures.

Annulus Fibrosis and an Anti-Growth Matrix

Figure 1:
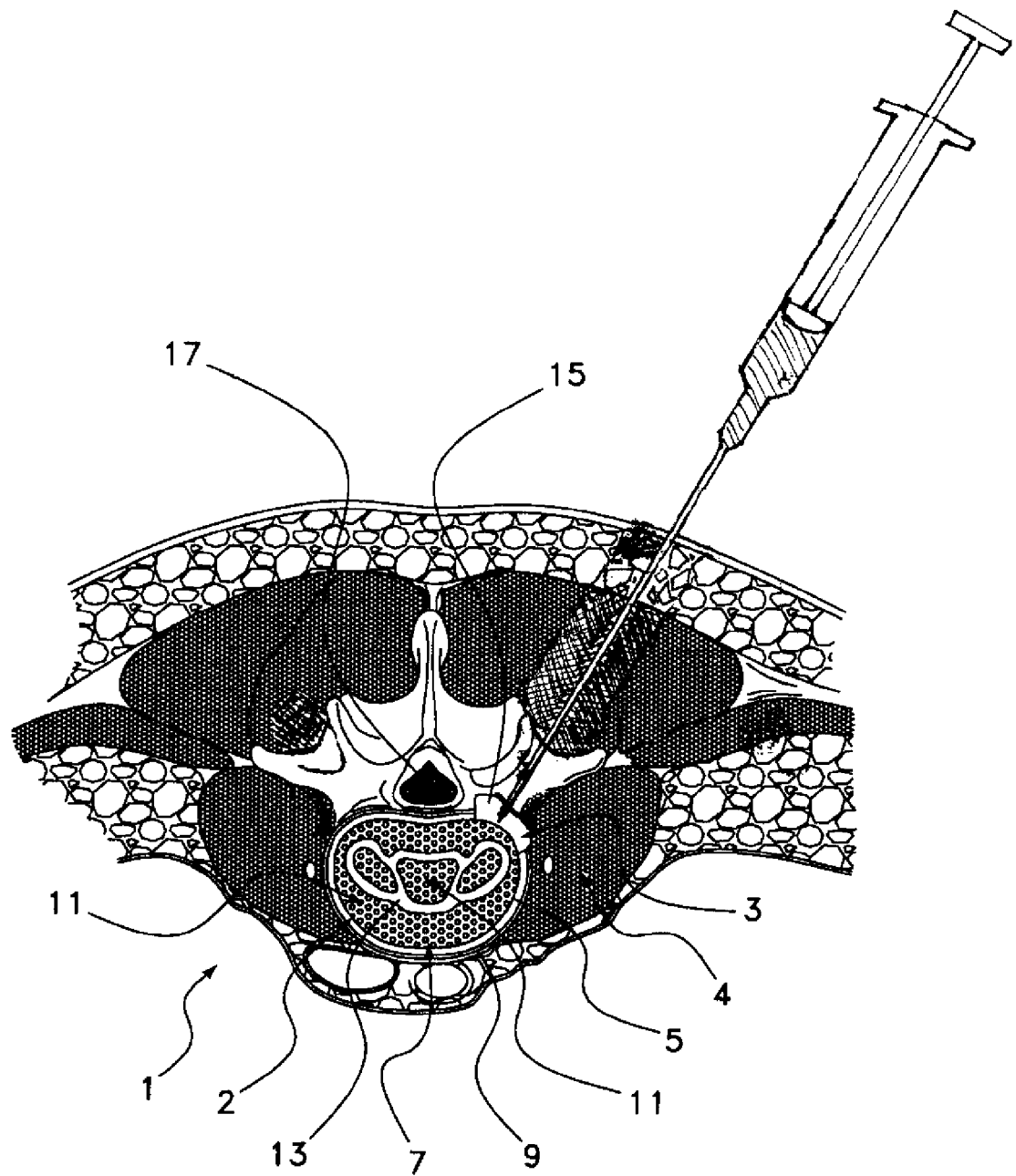
FIG. 1 is an axial cross-section view of a spinal assembly in one embodiment.

A method for closing a surgically prepared hole in the outer band of annulus fibrosis is shown in FIG. 1. FIG. 1 provides an axial view of a vertebral cross section 1 that is undergoing a spinal fusion procedure. A surgeon prepares a hole 3 in the posterior position of the outer annulus fibrosis band 5. The dimensions of the hole 3 are suitable for inserting various types of intervertebral disc implants 7 known in the art. For example U.S. Pat. No. 6,416,776 discloses an intervertebral disc implant that is a combination of human hair and block co-polymers that act as carriers for Bone Morphogenic Proteins; U.S. Pat. No. 6,969,404 discloses a device that is used for fortifying the inner walls of the annulus fibrosis with a self-expanding frame within a bag; U.S. Pat. No. 6,187,048 discloses an intervertebral disc implant that is made from conformable materials; U.S. Pat. Nos. 5,534,028 and 5,976,186 disclose a vertebral disc implant that is made of a hydrogel material; U.S. Pat. No. 5,645,597 discloses a method of intervertebral disc replacement that includes using a flexible prosthetic disc that expands once injected into disc space. For any of these implants 7 disclosed, or other such devices 7, the initial step is forming a hole 3 in the outer bands 5 of the annulus fibrosis 9, and the final steps involve sealing the hole 3.

The implant 7 may include growth agents and, in particular, may include osteogenic growth agents such as BMP (bone morphogenetic protein) and rhBMP, particularly BMP-2 and rhBMP-2; bFGF (basic fibroblast growth factor); IGF-1 (insulin-like growth factor); PDGF (platelet-derived growth factor); TGF-β1 (transforming growth factor beta 1); VEGF (vascular endothelial growth factor); GDF (growth and differentiation factor); and combinations thereof.

The implant 7 as shown in FIG. 1 may be a combination of natural bone graft 11 and an interbody device 13, in which the bone graft material 11 may include therapeutically effective amounts of one or more growth agents. The interbody device 13 may be located where the nucleous pulposus resided, and the bone graft 11 fills the remaining area 2 of the intervertebral disc space where normally there would be natural nucleous pulposus tissue. The implant 7 may act as a natural intervertebral disc and may provide a cushion and support for adjacent vertebrae. Although the method of the present invention refers to the implant 7 being associated with osteo-inductive factors to promote bone and tissue growth between adjacent vertebrae, the implant 7 can also be associated with other bioactive agents or, in the alternative, none of these materials.

After the surgeon inserts the various components 11, 13 of the implant 7 into the cleaned disc space 2, the hole 3 may be closed by delivery of a growth-inhibiting matrix 15 to the area in or about the hole 3. The matrix 15 can be a non-porous tissue adherent gel, a bio-resorbable polymer, or the like, that cures in vivo. In any event, the matrix 15 acts as a barrier, either physically or in combination with active components, to prevent or inhibit migration of tissue and growth factors from the region 2 associated with the implant 7.

The matrix 15 may be injected into the disc space located in the posterior section of the spine, for example the posterior region of the outer annulus fibrosis band 5 where the surgically prepared hole 3 is located, or, if the surgery is of the anterior sort, the outer anterior region of the annulus fibrosis band 5. The matrix 15 may be injected, for example, into the annular fibrosis 5 from the outer edge 9 of the annular fibrosis 5 to about 2 mm to about 5 mm into the annular fibrosis 5. This method may be well suited for interbody fusion procedures about the lumbar region of the spine, but it is within the scope of the invention whereby the matrix 15 can be used in other regions of the spine.

The surgeon can determine the amount of growth-inhibiting matrix 15 to deliver in order to sufficiently seal the surgically prepared hole 3. Preferably, the method includes delivery of enough matrix material 15 to seal the hole 3 such that the cured matrix 15 is larger in area than the size of the hole 3. Some portion of the matrix 15 may abut and cure onto healthy fibrocartilage associated with the outer annulus fibrosis band 5. The matrix 15 will seal the bio-environment 2 of the implant 7 from the epidural environment 4 of the spine or other bio-environments surrounding the vertebral body. The matrix 15 preferably only fills the open area of the annulus without penetration into the disc space beyond about 2 to 5 mm so as not to interfere with desired bone formation and fusion. The matrix 15 thus forms a barrier between two regions 2, 4. The first region 2 may extend from the outer bands of annulus fibrosis 9 into the center of the intervertebral disc space, where the implant 7 rests. Typically, bone tissue grows near the surfaces of the implant 7 in the first region 2. The implant 7 may have growth factors to encourage the formation of the selected tissue type, i.e. bone, such as those present within the bone graft 11, which may have BMP.

The matrix 15 may inhibit attachment of selected tissue cells, i.e. bone tissue, onto or into surfaces of the growth inhibiting matrix 15 by forming the matrix from anti-adhesive materials to prevent the same. Alternatively, the outer surfaces of the matrix 15, and particularly those regions of the outer surfaces that are exposed to the first region 2 in which growth of the selected tissue is desired, may be coated or otherwise provided with an anti-adhesive material.

Suitable Materials for the Anti-Growth Matrix

A suitable matrix 15 can be made, in whole or in part, from various materials, where non-limiting examples are bio-resorbable polymers, non-bio-resorbable polymers, natural polymers, anti-adhesion gels, and any combinations thereof.

Suitable examples of bio-resorbable polymers may include, without limitation: poly(alpha-hydroxy acids), poly (lactide-co-glycolide) (PLGA), polylactide (PLA), polyglycolide (PG), polyethylene glycol (PEG), conjugates of poly (alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, silk, and combinations thereof.

Suitable non-limiting examples of synthetic non-bio-resorbable polymers include hydrogels such as PVA, delrin, polyurethane, polyethylene, co-polymers thereof, and any combinations thereof.

The matrix 15 may be made from suitable anti-adhesion materials, which may include, without limitation, hyaluronic acid, carboxy methyl cellulose, gelatin, hydrogels, collagen gels, synthetic polymer formulations, and combinations thereof.

The matrix 15 may be made from natural polymers including, without limitations, collagen, elastin, silk, hyaluronic acid, chitosan, and any combinations thereof.

The growth-inhibiting matrix 15 may cure in vivo and may be bio-resorbable within a time frame that is sufficiently close to the time release of the osteo-inductive factors 11 associated with the implant 7, which may preferably be from about two to six weeks after delivery of the matrix 15 to the surgically prepared hole 3. However, a matrix 15 that seals the hole 3 for a longer time than stated may also be employed.

Additives Associated with Anti-Growth Matrix

In certain embodiments, the matrix 15 may include an agent to prevent cell attachment and infiltration. In certain embodiments, the agent to prevent cell attachment and infiltration may be an anionic polymer or polysaccharide. Suitable polysaccharides may include, without limitation, dextran sulfate and other carbohydrates.

In certain embodiments, the matrix 15 may include at least one anti-osteo-inductive antibody, anti-BMP antibody, or the like. The anti-osteo-inductive antibody, anti-BMP antibody, or the like may be embedded within the entire volume of the matrix material 15 upon in vivo curing or may be placed as an external coating on the matrix 15. It is preferred that the matrix 15 retains the anti-osteo-inductive antibody such that osteoinductive agents moving through the matrix from the disc space will be bound and inactivated to prevent bone formation beyond the matrix outside of the disc space.

Suitable anti-osteo-inductive antibodies may include without limitation anti-BMP, anti-BMP-2, anti-bFGF, anti-IGF-1, anti-PDGF, anti-rhBMP, anti-TGF-β1, anti-VEGF, anti-GDF antibodies, and any combinations thereof.

Dosage of Additives Associated with the Matrix

Typically, the bio-active additives within the matrix 15 will not be greater than about 1% to 10% of the total matrix 15 volume once cured in vivo. The additives can be added to the matrix 15 before or during delivery to the hole 3. Any suitable range for the bio-active additives may be used, and are typically in the range of about 0.01 mg per cc to about 100 mg per cc. In other embodiments, from about 0.1 mg per cc to about 50 mg per cc may be employ. In yet other embodiments, from about 0.1 mg per cc to about 20 mg per cc of a bio-active additive may be employed. In certain advantageous embodiments, about 1 to 3 mg of a growth factor (BMP, for example) per cc of carrier (for example purified collagen and a biphasic calcium phosphate (BCP)) may be sufficient, for example, to heal bone defects. Accordingly, a range of about 0.1 mg to about 12 mg of an osteo-inductive additive (BMP, for example) may be preferred for many intervertebral implants 7. As such, it may be desirable that the growth-inhibiting matrix 15 have anti-osteo-inductive additives in an amount sufficiently close to the 0.1 mg to about 12 mg of osteo-inductive additives associated with the intervertebral implant 7. One example embodiment of the matrix 15 comprises between about 2 mg and about 3 mg per cc, e.g., about 2.5 mg anti-adhesion gel/cc of carrier.

Delivery of Matrix into the Outer Annulus Fibrosis Band

After an implant 7 has been passed through a hole 3 in the outer portions of the annulus fibrosis 9 and inserted into a disc space 2, the hole 3 may be sealed by a mode of delivery that preferably achieves a local accumulation of the matrix 15 in or about the posterior portion of the annulus fibro-cartilage that abuts the spinal cord 17.

Delivery of an effective amount of the matrix 15 may be provided by a controlled administration system comprising a pump or similar device and an optional catheter connected to the pump to provide a channel for the matrix 15 to be transported from the pump to the targeted annulus fibrosis area 3, 9. The pump may provide for controlled release and deposition of the matrix 15 about the outer disc region, for example the posterior portion of the annulus fibrosis band 5 abutting the spinal cord, at a rate that substantially matches a targeted volumetric release rate profile selected by a surgeon.

A distal end of the catheter may be placed about the target area 3, 9. The matrix 15 may thus be directly released into the disc region associated with the hole 3 in the annulus fibrosis 9 that needs closing. The proximal end of the catheter may be fluidly connected to the pump. The pump is preferably disposed externally to the body while the matrix is delivered to the target area 3, 9, and may be provided with one or possibly more catheters to deliver the matrix 15 to appropriate target sites.

Other devices suited for drug delivery may also be used to seal the surgically prepared hole 3 about the outer portions of the annulus fibrosis 9. For example, a syringe may be a particularly advantageous delivery device for the matrix material 15.

To position the matrix 15 at the target region 3, 9, the distal end of the matrix delivery device, be it a catheter, a needle or the like and from which the matrix material 15 is ejected, is preferably positioned adjacent to the opening 3, a few centimeters away from the opening 3, or even up to about 5 mm into the opening 3. As the matrix material 15 is ejected from the distal end of the matrix delivery device, the surgeon may move the position of the distal end to dispose the matrix material 15 around the region of the opening 3, and even within the opening 3. A sufficient amount of matrix material 15 should be disposed in and around the opening 3 to provide an adequate seal.

EXAMPLE

Having generally described methods for using a growth inhibiting matrix to benefit intervertebral disc procedures, the following specific example is offered for purposes of illustration and only for illustration. There is no intention to limit the invention from the following words.

A method for using a growth inhibiting matrix for interbody spinal fusion may be prepared and delivered as follows. Exposure of the posterior annulus of the disc space to be treated is first achieved. Then, a hole is cut in the annulus, and a volume of disc material is removed to allow for placement of bone graft or bone graft substitute and interbody fusion device(s). After placement of the interbody fusion device, a growth-inhibiting matrix is applied from a syringe just inside the annulus opening and around the hole through which the interbody device was implanted.

Figure 2:
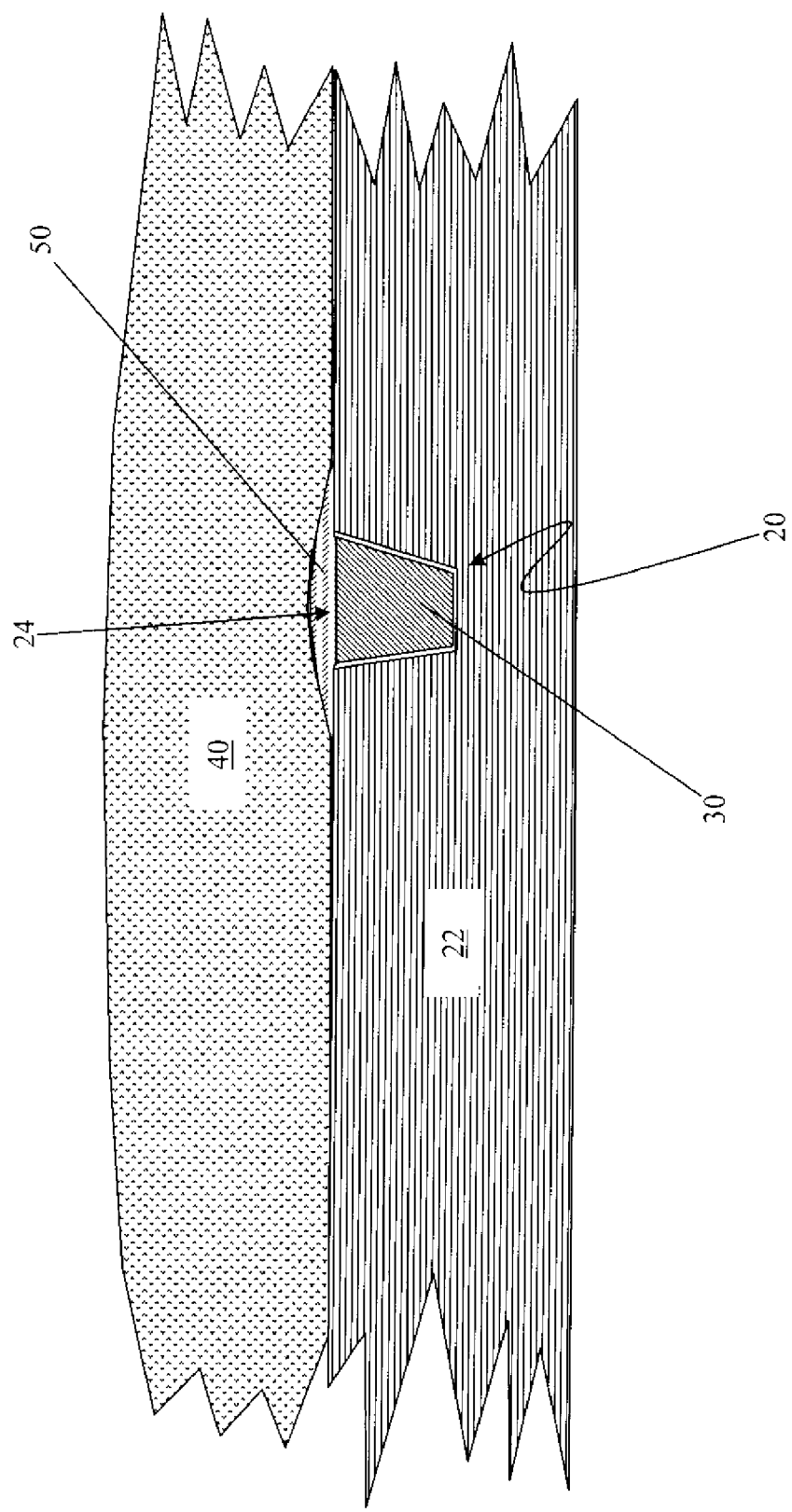
FIG. 2 depicts a longitudinal cross-section of soft tissue and sub-chondral bone with another embodiment of an osteogenic implant and growth-inhibiting matrix.

Another method of using the matrix of the present invention includes using the matrix to prevent unwanted migration of growth agents or cells from sub-chondral bone into hyaline cartilage tissue as shown in FIG. 2. A target site 20 for an implant 30 is identified. The target site 20 may be, for example, a defect in sub-chondral bone 22. The defect 20 may be a hole created by a surgeon, trauma, disease, or otherwise. It is desired that the defect 20 be surrounded by native bone 22.

An osteogenic implant 30, of any suitable type, is thus disposed within the defect 20. It is preferred that implant 30 completely fills the defect 20. The osteogenic implant 30 may include, for example, therapeutically effective amounts of an osteoinductive growth factor, such as rhBMP-2, embedded within a bioresorbable scaffolding, such as a mixture of collagen and calcium phosphate. As the scaffolding is absorbed by the host bone 22, the growth factor is released. High concentrations of the growth factor may encourage bone growth within the defect 20, thus encouraging the autologous bone 22 to migrate into and fill the defect 20; but, it can also induce bone formation within local soft tissue 40, which is not desired.

To prevent bone formation within the surrounding soft tissue 40, for example hyaline cartilage, a surgeon may dispose a growth-inhibiting matrix 50 over the opening 24 of the defect, such as by injecting the matrix 50 over the opening 24 after the implant 30 has been placed into the defect 20. The growth-inhibiting matrix 40 is thus positioned between the defect region 20, in which bone growth is desired, and the soft tissue region 40, in which bone growth is not desired.

The growth-inhibiting matrix 50 prevents migration of bone cells through the opening 24 and further prevents migration of the growth factors within the implant 30 into the soft tissue 40. The matrix may additionally be bioresorbable. As a result of the matrix 40, relatively high concentrations of the growth factors or agents may be kept within the defect 20 without causing undesired bone growth within the soft tissue 40.

The matrix may further comprise at least one inhibitory agent that blocks or antagonizes the growth effects of the growth agent, such as anti-BMP, anti-BMP-2, anti-bFGF, anti-IGF-1, anti-PDGF, anti-rhBMP, anti-TGF-β1, anti-VEGF, anti-GDF, and the like. The inhibitory agent may be disposed throughout the volume of the matrix 40.

Although the invention herein has been described with reference to particular embodiments, it is to be understood that these embodiments are merely illustrative of the principles and applications of the present invention. It is understood that many modifications may be made to the illustrative embodiments and that other arrangements may be devised without departing from the spirit and scope of the present invention as defined by the following claims.

What is claimed is:

1. A method for preventing unwanted tissue growth associated with an implant and growth agent, the method comprising:
   disposing an implant containing an effective amount of a growth agent embedded within the implant into a first region in which growth of a selected tissue type is desired, the implant having no osteogenic inhibitory agent;
   disposing a matrix between the first region and a second region in which growth of the selected tissue type is not desired, the matrix being separate from the implant and adapted to prevent the selected tissue type and growth agent from migrating between the first and second regions and the matrix is adapted to inhibit attachment of cells of the selected tissue type onto or into the matrix and the matrix contains no growth agent, wherein the matrix comprises at least one osteogenic inhibitory agent embedded within the entire volume of the matrix and selected from the group consisting of anti-BMP, anti-BMP-2, anti-bFGF, anti-IGF-1, anti-PDGF, anti-rhBMP, anti-TGF-β1, anti-VEGF, anti-GDF, and any combinations thereof, and the matrix is an anti-adhesion gel that cures in vivo; and
   allowing the matrix to cure in vivo.

2. The method of claim 1, wherein the matrix further comprises an effective amount of at least one bioactive molecule capable of inhibiting attachment of cells of the selected tissue type to a surface of the matrix that is exposed to the first region.

3. The method of claim 2, wherein the bioactive molecule capable of inhibiting cell attachment is an anionic polymer or polysaccharide.

4. The method of claim 1 wherein the growth agent is selected from the group consisting of BMP (bone morphogenetic protein), BMP-2 (bone morphogenetic protein), bFGF (basic fibroblast growth factor), IGF-1 (insulin-like growth factor), PDGF (platelet-derived growth factor), rhBMP (human recombinant bone morphogenetic protein), TGF-β1 (transforming growth factor beta 1), VEGF (vascular endothelial growth factor), GDF (growth and differentiation factor), and any combinations thereof.

5. The method of claim 1 wherein the matrix is fluid-permeable.

6. The method of claim 1, wherein the anti-adhesion gel is selected from the group consisting of hyaluronic acid, carboxy methyl cellulose, gelatin, hydrogel, collagen gel, synthetic polymer formulation, and combinations thereof.

7. The method of claim 1, wherein the matrix is disposed by injection.

8. The method of claim 1, wherein the matrix is bioresorbable within about 2 to 6 weeks.

9. The method of claim 8, wherein the bioresorbable matrix is selected from the group consisting of resorbable hydrogel, resorbable polymer composition, resorbable copolymer composition, resorbable polyion complex, fibrin, collagen, gelatin, alginate, hyaluronate, solubilized basement membrane preparation sold under the trademark MATRIGEL, Polyglycolide (PGA), glycolide-lactide copolymers (PGLA), polylactides (PLA), poly-L-lactide (PLLA), poly-D,L-lactide (PDLLA), ethylene oxide block copolymers with PLA, ethylene oxide block copolymers with propylene oxide chains, and any combination thereof.

10. The method of claim 1, wherein the selected tissue type is bone tissue.

11. The method of claim 1, wherein the implant comprises collagen and calcium phosphate.

\* \* \* \* \*